(12) United States Patent
Stevenson (10) Patent No.: US 8,567,730 B1
(45) Date of Patent: Oct. 29, 2013

(54) COLLAPSIBLE INTRAVENOUS FLUID POLE SYSTEM

(76) Inventor: Cherie Stevenson, Cerritos, CA (US)

( * ) Notice: Subject to any disclaimer, the term of this patent is extended or adjusted under 35 U.S.C. 154(b) by 0 days.

(21) Appl. No.: 13/603,683

(22) Filed: Sep. 5, 2012

(51) Int. Cl.
*A47F 5/00* (2006.01)
*A47F 7/00* (2006.01)

(52) U.S. Cl.
USPC ............... 248/125.8; 248/129; 248/188.7; 248/166

(58) Field of Classification Search
USPC ........... 248/166, 125.8, 129, 150, 188.7, 434, 248/170
See application file for complete search history.

(56) References Cited

U.S. PATENT DOCUMENTS

| | | | |
|---|---|---|---|
| 3,233,517 A * | 2/1966 | Morrison | 89/40.06 |
| 3,415,476 A * | 12/1968 | Mcdermott | 248/166 |
| 3,804,355 A * | 4/1974 | Uroshevich | 248/124.1 |
| 4,541,596 A | 9/1985 | Price | |
| 4,671,479 A * | 6/1987 | Johnson et al. | 248/173 |
| 4,744,536 A | 5/1988 | Bancalari | |
| 4,807,837 A * | 2/1989 | Gawlik et al. | 248/125.8 |
| 4,905,946 A * | 3/1990 | Wang | 248/170 |
| D310,570 S | 9/1990 | Wells | |
| 5,016,307 A | 5/1991 | Rebar | |
| 5,458,305 A * | 10/1995 | Woodward | 248/121 |
| 6,007,032 A * | 12/1999 | Kuo | 248/185.1 |
| D457,239 S | 5/2002 | Kunik | |
| 6,431,505 B2 | 8/2002 | Chinn et al. | |
| 7,735,789 B2 | 6/2010 | Blankenship et al. | |

* cited by examiner

*Primary Examiner* — Anita M King (57) ABSTRACT

A collapsible intravenous fluid pole system that can be easily stored or transported featuring a shaft with hangers disposed at the top end, the hangers being for attaching intravenous fluid bags, and legs pivotally attached at the bottom of the shaft. Wheels are disposed on the legs. The hangers can extend from the shaft or collapse to a storage position. The legs can extend or fold upwardly toward the shaft. The legs are attached via extension joints. A locking collar is disposed on the shaft. The locking collar can slide up and down along the shaft and can be inserted into a slot in the tongues of the legs to prevent the legs from folding upwardly to the folded position.

10 Claims, 10 Drawing Sheets

COLLAPSIBLE INTRAVENOUS FLUID POLE SYSTEM

BACKGROUND OF THE INVENTION

Intravenous fluid poles are large and cumbersome pieces of equipment, and they can be difficult to store and transport. The present invention features a novel intravenous fluid pole system that collapses and can be easily stored or transported. For example, the system features a telescopic pole and foldable legs. The intravenous fluid pole system of the present invention may be constructed in designs and styles to appeal to adults and/or children. The system of the present invention may include a storage bag or case.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Referring now to FIG. 1-7, the present invention features a novel intravenous fluid pole system (100) that collapses and can be easily stored or transported. The system (100) comprises a shaft (110) having a top end (111) and a bottom end (112). The shaft (110) can expand and contract to achieve a desired length. For example, the shaft (110) is a telescopic pole that can expand and contract in a standard manner. The shaft (110) can be secured at a particular desired length via a securing means (120), for example a nut that can be rotated in a first direction or a second direction to respectively allow or prevent expansion or contraction of the shaft (110), etc. Telescopic poles and securing means for telescopic poles are well know to one of ordinary skill in the art.

Figure 1:
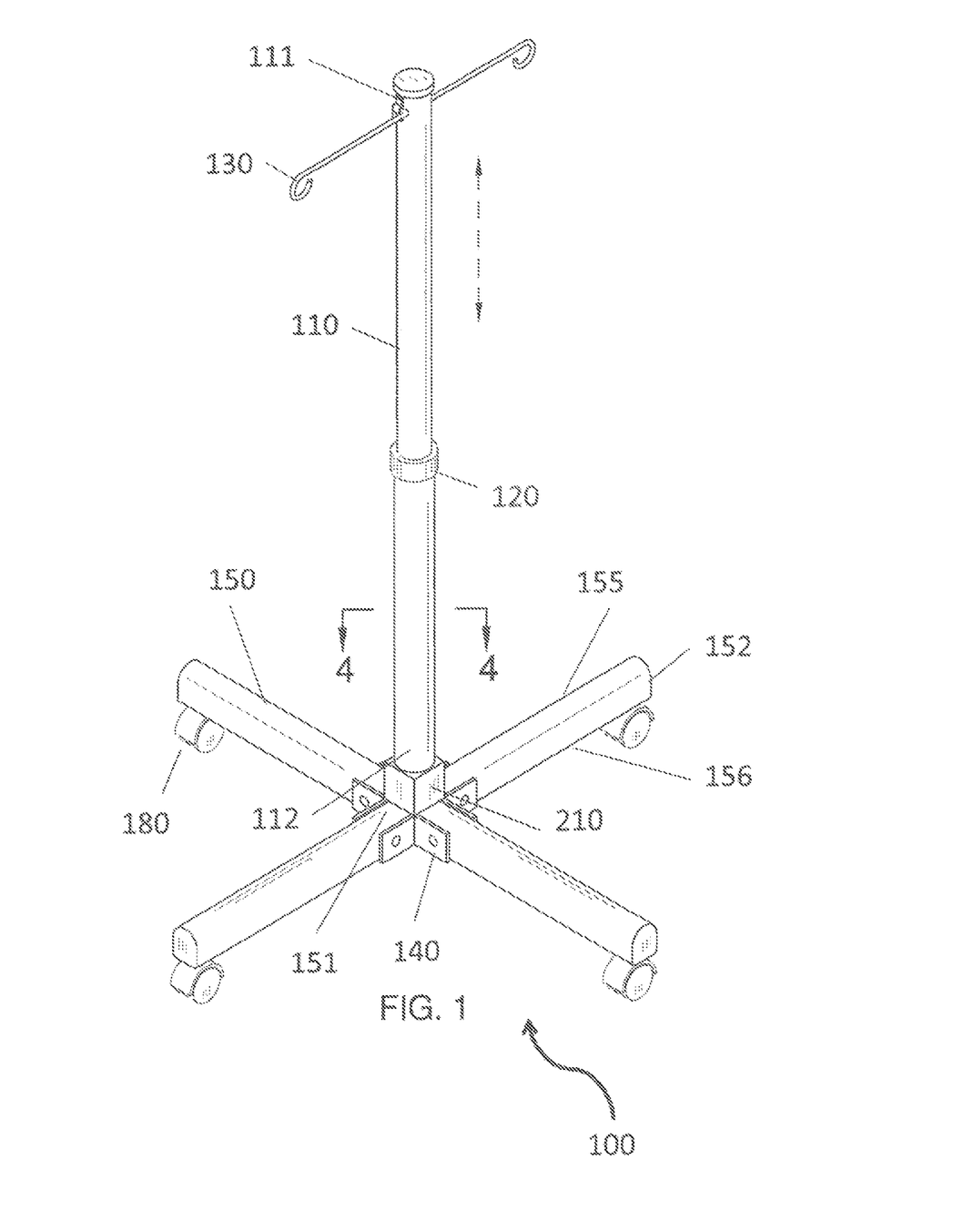
FIG. 1 is a perspective view of the system of the present invention.
Figure 2:
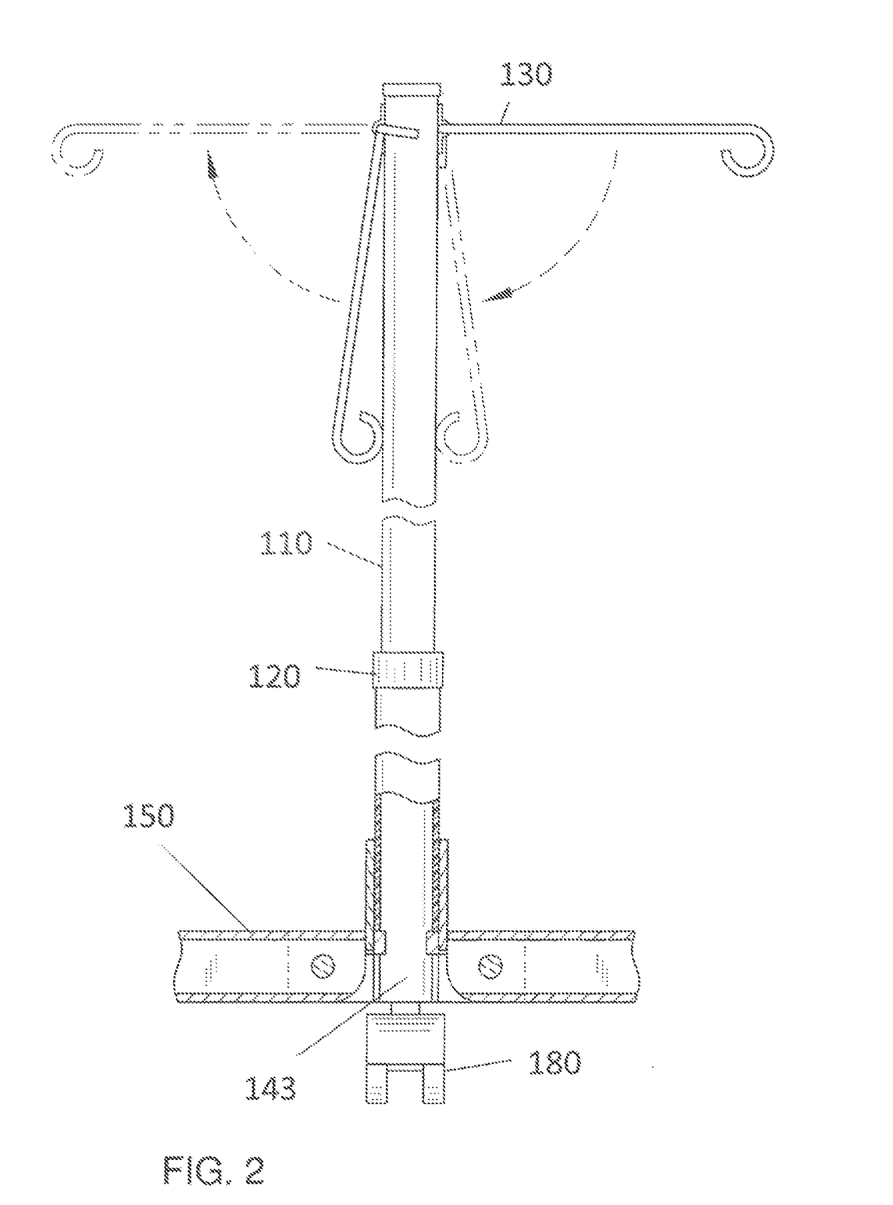
FIG. 2 is a side view of the system of the present invention.

The system (100) further comprises hangers (130) for attaching (e.g., temporarily attaching) intravenous fluid bags. For example, in some embodiments, a first hanger (130) is pivotally attached to the shaft (110) at or near the top end (111). In some embodiments, the system (100) comprises two hangers (130). In some embodiments, the system (100) comprises three or more hangers. The hangers (130) can move between at least an extended position and a collapsed position. FIG. 1 shows the hangers (130) in the extended position. In the extended position, the outer end of the hanger (130), e.g., the first hanger, is extended a distance from the shaft (110). FIG. 2 shows the collapsed position. In the collapsed position, the hanger (130), e.g., the first hanger, is positioned generally parallel to the shaft (110). The hanger (130), e.g., the first hanger, can be secured in the extended position or a position in between the extended position and the collapsed position.

Figure 1A:
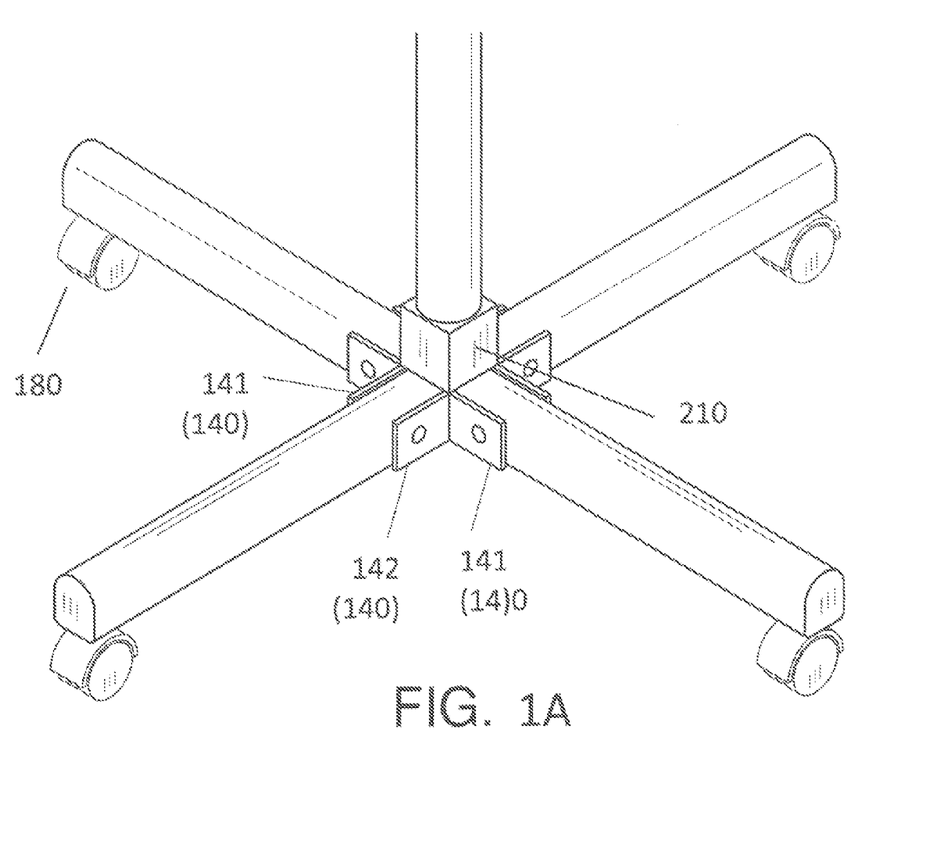
FIG. 1A is an enlarged view of FIG. 1.

Disposed at the bottom end (112) of the shaft (110) are at least three extender joints (140). In some embodiments, the system (100) comprises four extender joints (140). In some embodiments, the system (100) comprises more than four extender joints (140). The extender joints (140) are oriented symmetrically with respect to each other. As shown in FIG. 1A, the extender joints (140) each comprise a first panel (141) and a second panel (142) parallel to the first panel (141). The panels are spaced a distance apart. A hollow space (143) exists between the extender joints (140) (see FIG. 4).

The system (100) further comprises legs (150) with wheels (180), e.g., caster wheels. Each leg (150) is pivotally attached to an extender joint (140). Each leg (150) has a shaft end (151), an outer end (152) opposite the shaft end (151), a top surface (156), and a bottom surface (156) opposite the top surface (155). The shaft ends (151) of the legs (150) are each sandwiched between the first panel (141) and the second panel (142) of its respective extender joint (140).

Figure 2A:
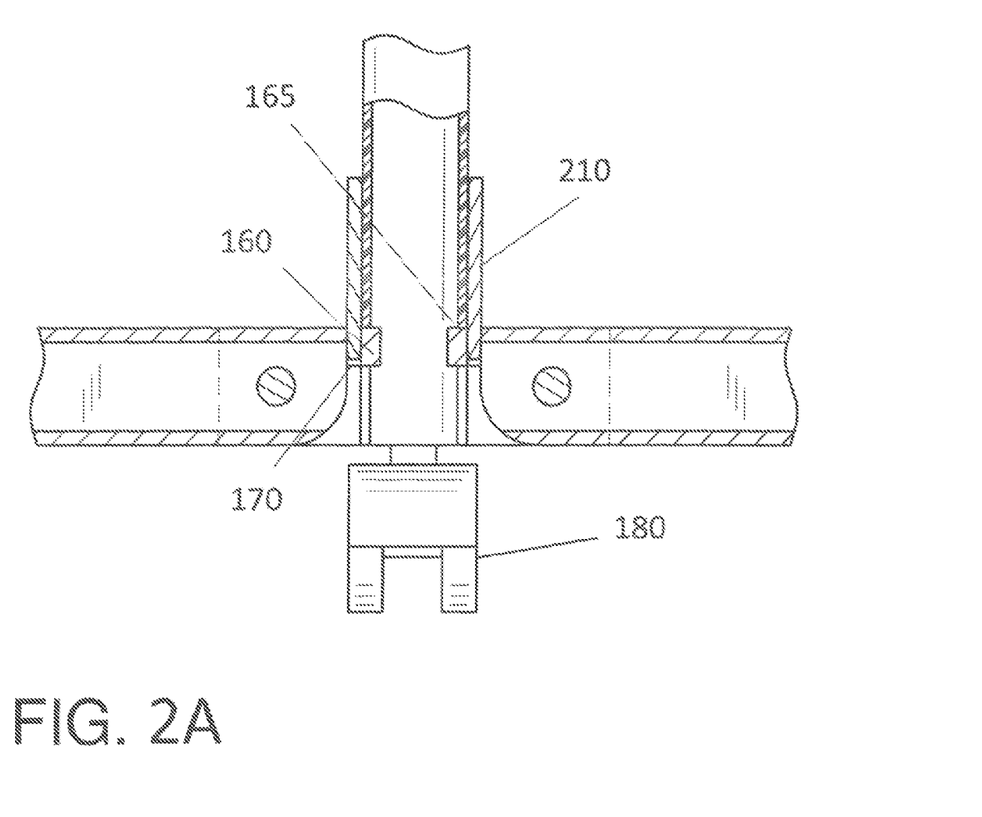
FIG. 2A is an enlarged view of FIG. 1.
Figure 8:
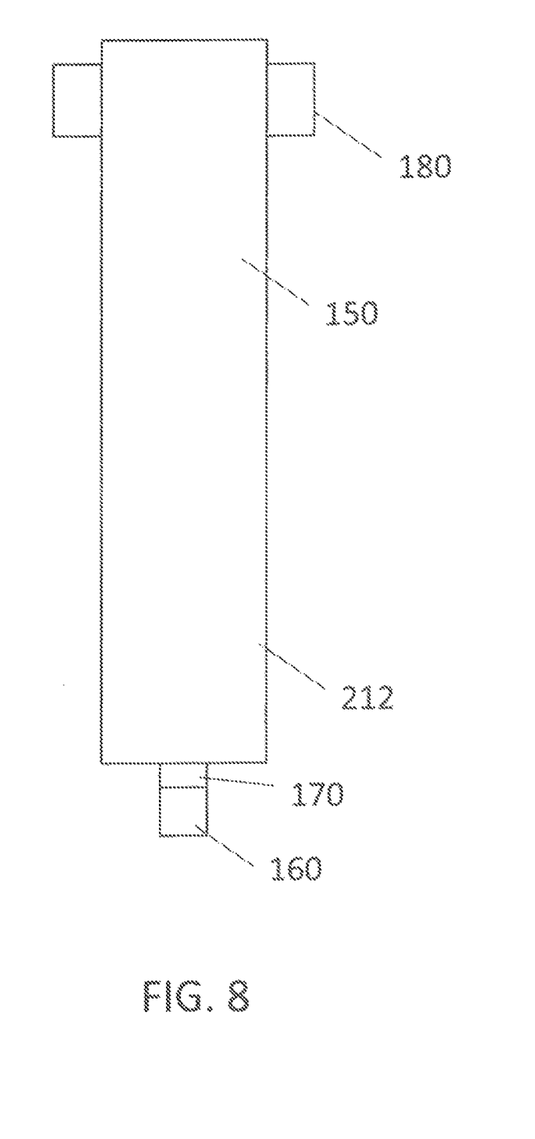
FIG. 8 is a top view of the system of the present invention.

As shown in FIG. 2A and FIG. 8, a joint tongue (160) extends from the top surface (155) of each leg (150) at the shaft end (151). The joint tongues (160) extend inwardly into the hollow space (143) between the extender joints (140). A slot (170) is disposed in the top surface (165) of the joint tongue (160) at an intersection of the shaft end (151) of the leg (150) and the joint tongue (160).

Figure 3:
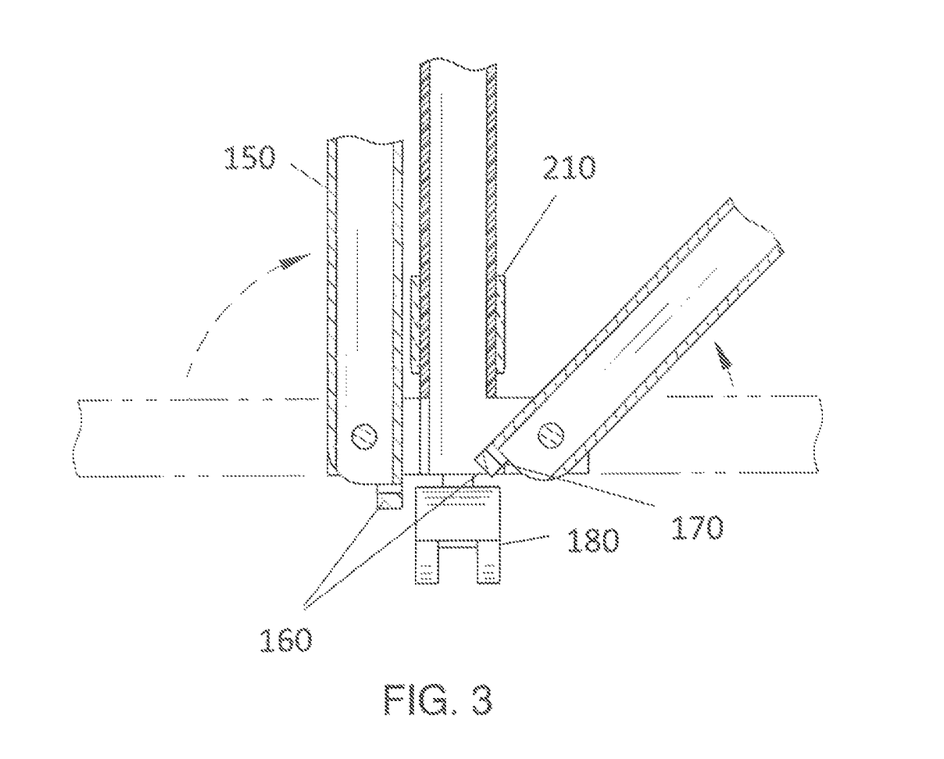
FIG. 3 is a detailed view of the system of the present invention.
Figure 4:
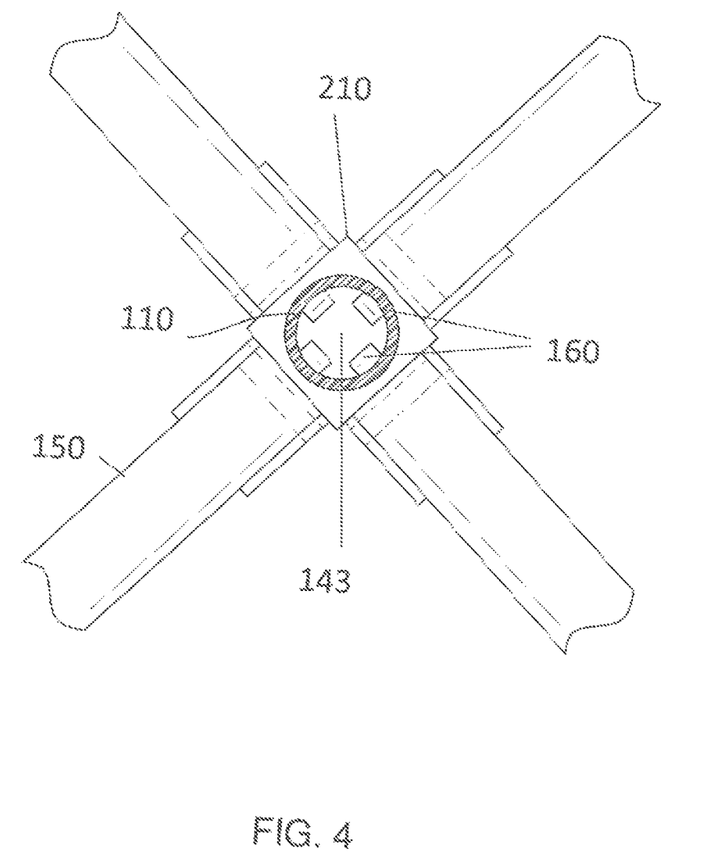
FIG. 4 is a top view of the system of the present invention.
Figure 5:
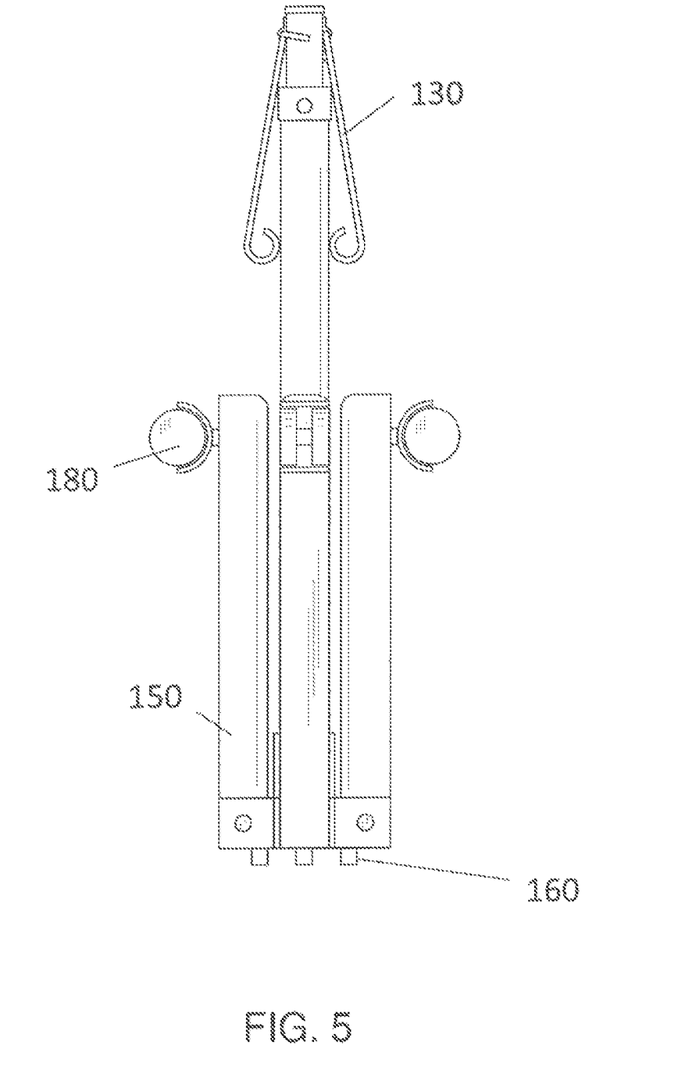
FIG. 5 is a side view of the system of the present invention.

The legs (150) can pivot between at least an extended position and a folded position by respectively pivoting the outer ends (152) of the legs (150) downwardly away from the shaft (110) and pivoting the outer ends (152) of the legs (150) upwardly toward the shaft (110). FIG. 2 and FIG. 2A shown the extended position. In the extended position the legs (150) extend outwardly from the shaft (110) so as to raise the extender joints (140) a distance above a ground surface and the joint tongues (160) protrude through the hollow space (143) in between the extender joints (140). FIG. 3 and FIG. 5 show the folded position. In the folded position, the legs (150) are pivoted upwardly such that the top surfaces (155) of the legs (150) face the shaft (110) and the joint tongues (160) face downwardly toward the ground surface.

The system (100) further comprises a locking collar (210) slidably and snugly disposed on the shaft (110) near the bottom end (112) of the shaft (110). The locking collar (210) can slide up and down along the shaft (110) between at least a locked position and an unlocked position. In the locked position, the locking collar (210) slides into the slots (170) in the joint tongues (160) and prevents the legs (150) from being able to pivot upwardly from the extended position to the folded position. In the unlocked position, the locking collar (210) is raised a distance above the slots (170) in the joint tongues (160) so that the legs (150) can freely pivot from the extended position to the folded position.

Figure 7:
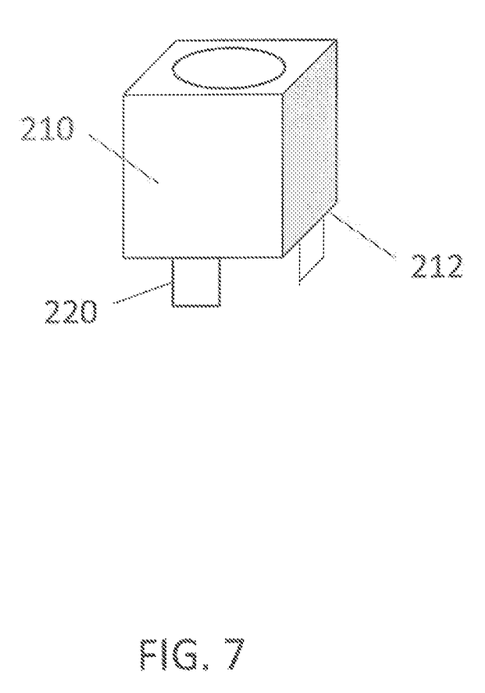
FIG. 7 is an alternative embodiment of the system of the present invention.

As shown in FIG. 7, in some embodiments, the locking collar (210) comprises collar tongues (220) that extend downwardly from the bottom end (212) of the locking collar (210). The collar tongues (220) are adapted to insert into the slots (170) of the joint tongues (160). The collar tongues (220) may insert into the slots (170) in lieu of the actual locking collar itself.

The system (100) of the present invention may be constructed in a variety of styles, colors, and designs. The system (100) of the present invention may be constructed in a variety of shapes. For example, in some embodiments, the shaft (110) has a rectangular cross section as viewed from the top end (111) and the locking collar (210) has a rectangular cross section as viewed from the bottom end (212). In some embodiments, the shaft (110) is cylindrical and the locking collar (210) is cylindrical. The system (100) is not limited to the aforementioned shapes and styles.

Figure 6:
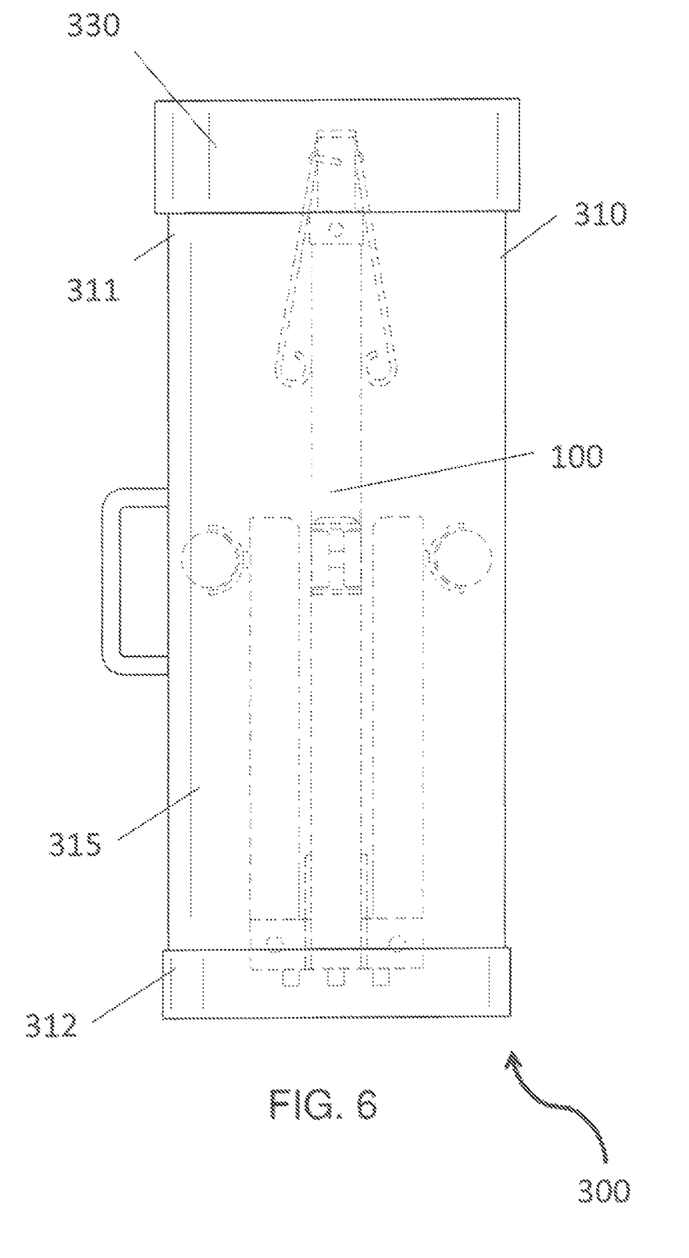
FIG. 6 is a storage view of the system of the present invention.

As shown in FIG. 6, in some embodiments, the system (100) further comprises a storage case (300). For example, the storage case (300) may comprise a base (310) having a first end (311), a second end (312), and an inner cavity (315). The shaft (110), the hanger (130) in the collapsed position, and the legs (150) in the folded position can be housed in the inner cavity (315) of the storage case (300). In some embodiments, the storage case (300) further comprises a removable cap (330) for sealing closed the inner cavity (315).

In some embodiments, the system (100) of the present invention is constructed from medical-grade plastic. Without wishing to limit the present invention to any theory or mechanism, it is believed that the medical-grade plastic can provide for the system (100) to be lightweight. The system (100) of the present invention is not limited to the aforementioned medical-grade plastic.

As used herein, the term "about" refers to plus or minus 10% of the referenced number.

The disclosures of the following U.S. Patents are incorporated in their entirety by reference herein. U.S. Pat. No. 3,804,355; U.S. Pat. No. 4,541,596; U.S. Pat. No. 4,744,536; U.S. Pat. No. 4,807,837; U.S. Design Pat. No. D310,570; U.S. Pat. No. 5,016,307; U.S. Design Pat. No. D457,239; U.S. Pat. No. 7,735,789.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has bean shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. A collapsible intravenous fluid pole system (100) comprising:
   (a) a shaft (110) having a top end (111) and a bottom end (112), the shaft (110) is a telescopic pole that can expand and contract in a standard manner, the shaft (110) can be secured at a particular desired length via a securing means (120);
   (b) a first hanger (130) pivotally attached to the shaft (110) at or near the top end (111), the first hanger (130) is adapted to temporarily hold an intravenous fluid bag, the first hanger (130) can move between at least an extended position and a collapsed position, in the extended position the first hanger (130) is extended a distance from the shaft (110) and in the collapsed position the first hanger (130) is positioned generally parallel to the shaft (110), the first hanger (130) can be secured in at least the extended position or a position in between the extended position and the collapsed position; and
   (c) at least three extender joints (140) disposed at the bottom end (112) of the shaft (110), the extender joints (140) are oriented symmetrically with respect to each other, the extender joints (140) each comprise a first panel (141) and a second panel (142) parallel to the first panel (141) and spaced a distance apart from the first panel (141), a hollow space (143) exists between the at least three extender joints (140);
   (d) a leg (150) pivotally attached to each extender joint (140), each leg (150) has a shaft end (151), an outer end (152) opposite the shaft end (151), a top surface (155), and a bottom surface (156) opposite the top surface (155), the shaft ends (151) of the legs (150) are each sandwiched between the first panel (141) and the second panel (142) of its respective extender joint (140), as joint tongue (160) extends from the top surface (155) of each leg (150) at the shaft and (151), the joint tongues (160) extend inwardly into the hollow space (143) between the at least three extender joints (140), wherein a slot (170) is disposed in a top surface (165) of the joint tongue (160) at an intersection of the shaft end (151) of the leg (150) and the joint tongue (160), the legs (150) can pivot between at least an extended position and a folded position by respectively pivoting the outer ends (152) of the legs (150) downwardly away from the shaft (110) and pivoting the outer ends (152) of the legs (150) upwardly toward the shaft (110), in the extended position the legs (150) extend outwardly from the shaft (110) so as to raise the extender joints (140) a distance above a ground surface and the joint tongues (160) protrude through the hollow space (143) in between the at least three extender joints (140), and in the folded position the legs (150) are pivoted upwardly such that the top surfaces (155) of the legs (150) face the shaft (110) and the joint tongues (160) face downwardly toward the ground surface;
   (e) a locking collar (210) slidably and snugly disposed on the shaft (110) near the bottom end (112) of the shaft (110), the locking collar (210) can slide up and down along the shaft (110) between at least a locked position and an unlocked position, in the locked position the locking collar (210) slides into the slots (170) in the joint tongues (160) and prevents the legs (150) from being able to pivot upwardly from the extended position to the folded position, in the unlocked position the locking collar (210) is raised a distance above the slots (170) in the joint tongues (160) so that the legs (150) can freely pivot from the extended position to the folded position; and
   (f) a wheel (180) disposed on the bottom surface (156) of each leg (150).

2. The system (100) of claim 1, wherein the securing means (120) comprises a nut (122) that can be rotated in a first direction or a second direction to respectively allow or prevent expansion or contraction of the shaft (110).

3. The system (100) of claim 1, wherein the wheel (180) is a caster wheel.

4. The system (100) of claim 1 further comprising a storage case (300), the storage case (300) comprising a base (310) having a first end (311), a second end (312), and an inner cavity (315), the shaft (110), the hanger (130) in the collapsed position, and the legs (150) in the folded position are housed in the inner cavity (315) of the storage case (300).

5. The system (100) of claim 4, wherein the storage case (300) further comprises a removable cap (330) for sealing closed the inner cavity (315).

6. The system (100) of claim 1 comprising two or more hangers (130).

7. The system (100) of claim 1 comprising an intravenous fluid bag attached to the hanger (130).

8. The system (100) of claim 1, wherein the locking collar (210) comprises collar tongues (220) extending downwardly from a bottom end (212) of the locking collar (210), the collar tongues (220) are adapted to insert into the slots (170) of the joint tongues (160).

9. The system (100) of claim 1, wherein the shaft (110) has a rectangular cross section as viewed from the top end (111), and the locking collar (210) has a rectangular cross section as viewed from the bottom end (212).

10. The system (100) of claim 1, wherein the shaft (110) is cylindrical, and the locking collar (210) is cylindrical.

\* \* \* \* \*